United States Patent [19]
Raab

[11] Patent Number: 4,792,613
[45] Date of Patent: Dec. 20, 1988

[54] POLYFLUORINATED CYCLIC CARBONATES

[75] Inventor: Klaus Raab, Burgkirchen, Fed. Rep. of Germany

[73] Assignee: Hoechst Aktiengesellschaft, Frankfurt am Main, Fed. Rep. of Germany

[21] Appl. No.: 69,054

[22] Filed: Jul. 2, 1987

[30] Foreign Application Priority Data

Jul. 4, 1986 [DE] Fed. Rep. of Germany ....... 3622534

[51] Int. Cl.$^4$ .......................................... C07D 317/36
[52] U.S. Cl. .................................................. 549/229
[58] Field of Search ........................................ 549/229

[56] References Cited

U.S. PATENT DOCUMENTS 3,455,954 7/1969 Prager .
3,870,748 3/1975 Katsushima et al. ............... 549/563
4,073,817 2/1978 Jager ................................... 549/563

OTHER PUBLICATIONS

S. Benefice et al. *Tetrahedron* 40, 1541–1544 (1984).
Moore, L. David, "Radical Addition...", *J. Chem. and Engineering Data* 9, 251–254 (1964).

*Primary Examiner*—Norma S. Milestone

[57] ABSTRACT

Novel polyfluorinated cyclic carbonates of the formula $$R_F-CH_2-CH-CH_2$$
$$\phantom{R_F-CH_2-}| \phantom{-CH-}|$$
$$\phantom{R_F-CH_2-}O \phantom{-CH-}O$$
$$\phantom{R_F-CH_2-C}\diagdown \diagup$$
$$\phantom{R_F-CH_2-CHC}C$$
$$\phantom{R_F-CH_2-CHC}\|$$
$$\phantom{R_F-CH_2-CHC}O$$

in which $R_F$ is an unbranched or branched perfluoroalkyl radical having 1 to 18 carbon atoms, an unbranched or branched ω-hydro- or ω-haloperfluoroalkyl radical having 1 to 18 carbon atoms, or a cycloperfluoroalkyl radical having 4 to 6 carbon atoms, are described. They are prepared by reacting a polyfluorinated halohydrin of the formula $R_F-CH_2-CH(Hal)-CH_2OH$, in which $R_f$ has the meaning mentioned and Hal represents a halogen, with carbonate or hydrogen carbonate compounds in the presence of an aprotic solvent. The novel compounds, which are generally solid and crystalline at room temperature, represent, in particular, good waterproofing and oil-proofing agents for textiles.

3 Claims, No Drawings

POLYFLUORINATED CYCLIC CARBONATES

The invention relates to novel polyfluorinated cyclic carbonates, a process for the preparation of these, and the use of these.

U.S. Pat. No. 3,455,954 discloses perfluorinated cyclic carbonates of the following formula, in which $R_f$ is a perfluoroalkyl radical:

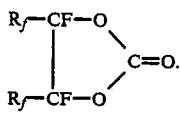

These completely fluorinated organic carbonates are obtained by fluorination of the corresponding H-containing cyclic carbonates.

In the journal "Tetrahedron", Vol. 40, No. 9, pages 1541 to 1544, 1984, the reaction of $R_fZnI$ ($R_f$=perfluoroalkyl) with ethylene carbonate according to the following reaction equation is described, an ethylene carbonate which is substituted by a perfluoroalkyl radical being produced, inter alia:

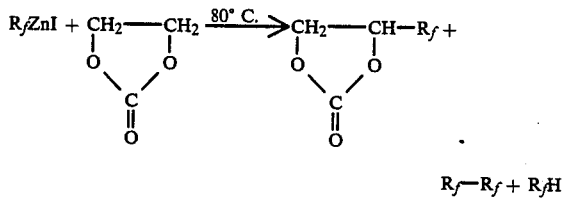

$$R_f-R_f + R_fH$$

However, the poyfluorinated cyclic carbonate is only produced with a yield of about 5%, whereas the compound $R_fH$ makes up 90% of the reaction product.

The object of the present invention is to provide novel polyfluorinated cyclic carbonates and to develop a process for the preparation thereof with which the novel compounds are obtained in a relatively large yield.

The polyfluorinated cyclic carbonates according to the invention correspond to the following formula I

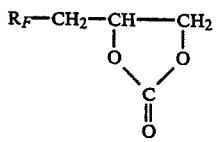

in which $R_F$ is an unbranched or branched perfluoroalkyl radical having 1 to 18 carbon atoms, an unbranched or branched ω-hydro- or ω-haloperfluoroalkyl radical having 1 to 18 carbon atoms, or a cycloperfluoroalkyl radical having 4 to 6 carbon atoms.

The ω-halogen is preferably bromine or iodine. The unbranched (straight-chain) or branched perfluoroalkyl radical and, likewise, the ω-hydro- or ω-haloperfluoroalkyl radical contain 1 to 18 carbon atoms, preferably 3 to 14 and in particular 6 to 12 carbon atoms. Examples of such radicals are: $CF_3$—, $CF_3$—$CF_2$—, $(CF_3)_2CF$—, $CF_3$—$(CF_2)_3$—, $CF_3$—$(CF_2)_N$—, in which n is 5, 6, 7, 8, 9, 11, 13 or 15, $(CF_3)_2CF$—$(CF_2)_2$—, $(CF_3CF_2CF_2)(CF_3)_2C$—, $(CF_3)_2CF$—$(CF_2)_4$—, $HCF_2$—$CF_2$—, $HCF_2$—$(CF_2)_3$—; $HalCF_2$—$CF_2$—, $HalCF_2$—$(CF_2)_3$—, $HalCF_2$—$(CF_2)_5$—and $HalCF_2$—$(CF_2)_7$—, in which Hal is bromine or iodine. The cycloperfluoroalkyl radical is preferably the cycloperfluoropentyl radical or the cycloperfluorohexyl radical.

The preferred meaning of $R_F$ in the formula I is that of an unbranched or branched perfluoroalkyl radical, the unbranched perfluoroalkyl radicals being particularly preferred.

The polyfluorinated cyclic carbonates according to the invention are generally substances which are colorless, solid and crystalline at room temperature.

The process, according to the invention, for the preparation of the novel polyfluorinated cyclic carbonates of the formula I has the characterizing feature that a polyfluorinated halohydrin of the following formula II

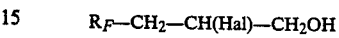

$$R_F-CH_2-CH(Hal)-CH_2OH$$

in which $R_F$ has the abovementioned meaning and Hal represents a halogen, preferably bromine or iodine, is reacted with an alkali metal carbonate, an alkali metal hydrogen carbonate or an alkylammonium hydrogen carbonate in the molar ratio 1:1 to 2 in the presence of an aprotic solvent, with the proviso that, when an alkali metal carbonate or hydrogen carbonate is used, the reaction is carried out at a temperature of 25° to 100° C., preferably 40° to 80° C., and when an alkylammonium hydrogen carbonate is used, the reaction is carried out at a temperature of −20° to 40° C., preferably −10° to 20° C., and the intended compound (that is, the compound according to the formula I) is isolated from the reaction product.

The preparation of the compounds according to the invention for example in the case of sodium hydrogen carbonate as the second reaction component—is based on the following reaction equation:

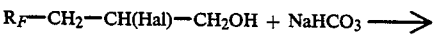

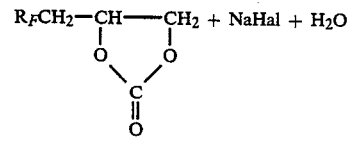

in which $R_F$ and Hal have the abovementioned meaning. one of the two starting compounds (1st reaction component) is thus a polyfluorinated halohydrin of the formula II above, in which Hal is a halogen, preferably bromine or iodine, and that which has been stated regarding $R_F$ of the formula I applies to $R_F$. The halohydrin employed can also be a mixture of different $R_F$ radicals, preferably different perfluoroalkyl radicals. The other starting compound (2nd reaction component) is one of the above-mentioned carbonate or hydrogen carbonate compounds. The alkali metal in these compounds is preferably potassium or sodium, sodium being particularly preferred. The alkyl radical in the alkylammonium hydrogen carbonates is preferably a $C_1$ to $C_4$-alkyl group and in particular methyl or ethyl. Of the alkylammonium hydrogen carbonates, the tetraalkylammonium hydrogen carbonates are preferred. Both the starting compounds to be employed in the process according to the invention have long been known.

According to the reaction equation given above, the two starting compounds are to be employed in the molar ratio 1:1. It has proven expedient to employ an excess of the 2nd reaction component, the carbonate or hydrogen carbonate compound. The molar ratio between the polyfluorinated halohydrin and the carbonate or hydrogen carbonate is according 1:1 to 2, preferably 1:1 to 1.5.

The reaction according to the invention is carried out in the presence of an aprotic solvent. Suitable aprotic solvents are dimethylformamide, dimethylacetamide, N-methylpyrrolidone, dimethyl sulfoxide, sulfolane, tetramethylurea, hexamethylphosphoric triamide, acetonitrile, monoethylene glycol dimethyl ether or diethylene glycol dimethyl ether.

It has been found that dimethylformamide and N-methylpyrrolidone are particularly suitable solvents when using an alkali metal carbonate and an alkali metal hydrogen carbonate as the 2nd reaction component, and acetonitrile is the particularly suitable solvent when using an alkylammonium hydrogen carbonate. The amount of solvent in which the polyfluorinated halohydrins are essentially soluble and the carbonates and hydrogen carbonates are virtually insoluble can vary within broad limits. For reasons of expediency, sufficient solvent is used so that a readily stirrable suspension of the halohydrin, carbonate or hydrogen carbonate and solvent employed is present. In general, 0.1 to 15 liters, preferably 0.3 to 6 liters, of solvent are employed per mole of polyfluorinated halohydrin.

With reference to the reaction temperature in the process according to the invention, it has been found that this is in different regions depending on the type of the 2nd reaction component and, in particular, must not exceed a certain maximum value. When using an alkali metal carbonate or alkali metal hydrogen carbonate as the 2nd reaction component, the reaction temperature must not exceed about 100° C. This is because, at a temperature above about 100° C., decomposition and/or conversion of the formed and intended compounds increases relatively quickly with increasing temperature. In the case of an alkali metal carbonate and an alkali metal hydrogen carbonate as the 2nd reaction component, the reaction temperature is accordingly 25° to 100° C., preferably 40° to 80° C. Although temperatures below about 25° C. are possible, the reaction times become disproportionately long. When using an alkylammonium hydrogen carbonate as the 2nd reaction component, the reaction temperature must not exceed about 40° C. since, as in the case of the carbonate and hydrogen carbonate compounds, decomposition and/or conversion of the formed and intended compounds occurs at elevated temperatures. The reaction temperature is accordingly −20° C. to +40° C., preferably −10° C. to +20° C. The reaction time is already disproportionately long at a temperature of below −20° C. In the reaction according to the invention, the reaction time, which depends essentially on the reaction temperature, is in the range 1 to 30 hours.

The manner in which the reaction according to the invention is generally carried out is that the starting compounds and the solvent are introduced into a reaction vessel, and the suspension obtained is brought to the reaction temperature with stirring, whereupon the reaction proceeds. In the case of reaction temperatures which are below room temperature, the starting compounds, the solvent and the suspension are correspondingly cooled. The course and end of the reaction can be followed, for example, by NMR spectroscopy. It has proven expedient to maintain a carbon dioxide atmosphere in the reaction vessel. This can be achieved, for example, by blowing, continuously or intermittently, a gentle stream of carbon dioxide through the suspension or the free space in the reaction vessel.

In order to isolate the intended compounds according to the invention after completion of the reaction, the reaction product is freed, for example by filtration or distillation, of unintended compounds, such as inorganic or organic salts, for example NaI and N(CH$_3$)$_4$I, excess carbonate or hydrogen carbonate, and distillable by-products, and water is added to the filtrate, distillation residue or distillate obtained, whereupon the intended compound precipitates out and is separated off. For purification, the resultant compounds according to the invention can be washed with water and recrystallized once or repeatedly.

The polyfluorinated cyclic carbonates, according to the invention, of the general formula I are suitable for oilproof and/or waterproof finishing of textile materials. They are furthermore suitable as surface-active auxiliaries, for example as an additive to waxes, fats and oils. The carbonates according to the invention furthermore represent products for the preparation of valuable fluorine compounds or fluorinated polymers. Thus, they react in the presence of catalytic amounts of bases, preferably in the presence of a catalytic amount of alkali metal hydroxides, such as KOH and NaOH, alkali metal carbonates, such as K$_2$CO$_3$ and Na$_2$CO$_3$, alkali metal hydrogen carbonates, such as KHCO$_3$ and NaHCO$_3$, tetraalkylammonium hydrogen carbonates, such as tetramethylammonium hydrogen carbonate, and tertiary amines, such as triethylamine, to form (perfluoroalkyl)propenols of the formula RF—CH=CH—CH$_2$OH, in which R$_F$ has the abovementioned meaning. This reaction proceeds in good yield. It represents an advantageous route for the preparation of the propenols mentioned, which are desirable starting compounds for the preparation of partially fluorinated polyacrylates, which represent good water-proofing and oilproofing agents. Furthermore, the carbonates according to the invention react with water, catalyzed by bases, to form (perfluoroalkyl)propanediols of the formula R$_F$—CH$_2$—CH(OH)—CH$_2$OH, in which R$_F$ has the abovementioned meaning; this is a very simple route for the preparation of fluorinated diols. On the other hand, the carbonates according to the invention represent suitable comonomers for modifying polymers, for example for modifying ethylene carbonate/terephthalic acid copolymers.

Of the mentioned uses of the compounds according to the invention, the preparation of the (perfluoroalkyl)propenols mentioned and the oilproofing and/or waterproofing of textiles are particularly important. Suitable textiles are, in particular, those made from natural and/or regenerated cellulose, such as cotton, linen, viscose staple fiber and cellulose acetate, and those made from wool. Textiles made from, for example, nylons, polyesters, polyacrylonitrile or polypropylene, or textiles made from mixtures of the rroducts mentioned, can also be employed. The textile material can be present, for example, as fibers, filaments or a fabric. The compounds are applied by conventional procedures, for example by dipping in appropriate solvent liquors, or by pad-mangling, spraying or padding. The compounds according to the invention are applied in an amount from 0.05 to 10% by weight, preferably 0.1 to 5% by weight, relative to the weight of the textile material. They impart an excellent waterproofing and oilproofing to the textile materials.

The invention is now illustrated in greater detail with reference to examples.

EXAMPLE 1

The compound, according to the invention, of the following formula Ia is prepared:

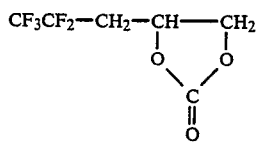

17.6 g (0.21 mol) of $NaHCO_3$, 60.8 g (0.20 mol) of $CF_3CF_2-CH_2-CHI-CH_2OH$ and 350 ml of dimethylformamide are introduced into a 1 liter three-necked flask fitted with reflux condenser, stirrer and internal thermometer. The supension is heated to 80° C. with stirring and kept at this temperature for 16 hours with stirring, after which time the reaction is complete. The flask contents are cooled to room temperature and filtered. About 0.5 liter of water is added to the filtrate, and the deposited precipitate is filtered off under suction, washed with water and dried in a desiccator in an oil-pump vacuum over $P_4O_{10}$. The product thus obtained corresponding to formula Ia above is colorless to pale yellow and has a melting point of 83° C. and a boiling point of 130° to 135° C. at 20 mbar. The yield is 63% of theory by weight. After purifying the product by recrystallization from $CCl_4$, its melting point is 84° C.

EXAMPLE 2

The compound, according to the invention, of the following formula Ib is prepared:

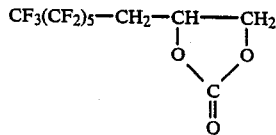

100.8 g (0.20 mol) of $C_6F_{13}-CH_2-CHI-CH_2OH$, 28.4 g (0 21 mol) of $N(CH_3)_4HCO_3$ and 900 ml of anhydrous acetonitrile—in each case cooled to −7° C.—are introduced into a 1 liter three-necked flask fitted with $CaCl_2$tube, stirrer and internal thermometer, and the suspension is brought to −5° C. with stirring. After a gentle stream of $CO_2$ has been passed through the suspension for 10 minutes in order to produce a $CO_2$ atmosphere, the suspension is kept at −5° C. for 20 hours with further stirring, after which time the reaction is complete. The flask contents are brought to room temperature and filtered under suction (removal of sparingly soluble $N(CH_3)_4I$). About 1 liter of water is added to the filtrate, and the deposited precipitate is filtered off under suction, washed with water and subsequently with diethyl ether in order to remove any organic by-products which may be present, and dried in vacuo. The product thus obtained, corresponding to the formula Ib above, is colorless and has a melting point of 118° C. (recrystallization from $CHCL_3$). The yield is 82% of theory by weight.

EXAMPLE 3

The compound, according to the invention, of the following formula Ic is prepared:

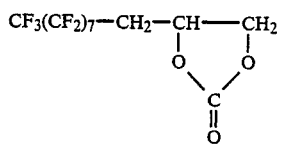

28.4 g (0.21 mol) of $N(CH_3)_4HCO_3$, 120.8 g (0.20 mol) of $C_8F_{17}-CH_2-CHI-CH_2OH$ and 700 ml of acetonitrile are introduced into a 4 liter three-necked flask equipped with reflux condenser and $CaCl_2$-tube, stirrer and internal thermometer. The suspension is cooled to 10° C., and a gentle stream of $CO_2$ is passed through the suspension for 10 minutes. The suspension is now kept at 8° to 10° C. for 12 hours, with stirring, after which time the reaction is complete. 2 liters of water are added to the flask contents. After brief stirring, the colorless precipitate, essentially comprising $N(CH_3)_4I$ and the intended compound according to the invention, is allowed to settle. The supernatant solution is eecanted and filtered. In order to remove tee $N(CH_3)_4I$, the precipitate is washed several times with water and subsequently with acetonitrile, and thereafter dried in vacuo. The product thus obtained, corresponding to the formula Ic above, is colorless and has a melting point of 136° C. (recrystallization from $CHCl_3$). The yield is 74% of theory by weight.

EXAMPLE 4

The compound, according to the invention, of the following formula Id is prepared:

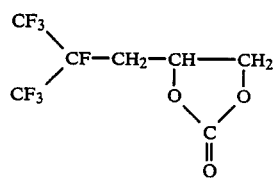

29.4 g (0.35 mol) of $NaHCO_3$, 88.5 g (0.25 mol) of $(CF_3)_2CF-CH_2-CHI-CH_2OH$ and 400 ml of dimethylformamide are introduced into a 1 liter three-necked flask fitted with reflux condenser, stirrer and internal thermometer. The suspension is heated to 80° C. with stirring and kept at this temperature for 18 hours with stirring, after which time the reaction is complete. The flask contents are cooled to room temperature and filtered. 0.7 liter of water is added to the filtrate. The lower liquid phase is separated off in a separating funnel, extracted by shaking with water, and distilled in a water-pump vacuum. The product thus obtained, corresponding to the formula Id above, is colorless and has a boiling point of 17°-120° C. at 10 mbar. Its melting point is 26° C. The yield is 52% of theory by weight.

EXAMPLE 5

The compound, according to the invention, of the following formula Ie is prepared:

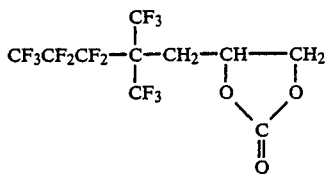

4.4 g (52 mmol) of $NaHCO_3$, 22.9 g (50 mmol) of $CF_3CF_2CF_2(CF_3)_2C$—$CH_2$—$CHBr$—$CH_2OH$ and 150 ml of dimethylformamide are introduced into a 500 ml three-necked flask fitted with reflux condenser, stirrer and internal thermometer. The suspension is heated to 80° C. with stirring and kept at this temperature for 20 hours with stirring, after which tmme the reaction is complete. The flask contents are cooled to room temperature and filtered. About 0.2 liter of water is added to the filtrate. The lower liquid phase is separated off in a separating funnel. The lower liquid phase becomes solid after further washing with water. This solid is filtered off under suction, washed with water and subsequently with a little diethyl ether, and thereafter dried in vacuo. The product thus obtained, corresponding to the formula Ie above, is colorless and has a melting point of 58° C. The yield is 66% of theory by weight.

EXAMPLE 6

The compound, according to the invention, of Example 2, that is the compound of formula Ib, is prepared. 15.9 g (0.15 mol) of $Na_2CO_3$, 50.4 g (0.10 mol) of $CF_3(CF_2)_5$—$CH_2$—$CHI$—$CH_2OH$ and 300 ml of dimethylformamide are introduced into a 500 ml three-necked flask fitted with reflux condenser, stirrer and internal thermometer. The suspension is heated to 80° C. with stirring and kept at this temperature for 16 hours with stirring. The flask contents are cooled to room temperature and filtered. 0.5 liter of water is added to the filtrate. The deposited precipitate is filtered off under suction, washed with water and subsequently with diethyl ether and dried in vacuo. The product thus obtained, corresponding to the formula Ib, has the properties specified in Example 2. The yield is 61% of theory by weight.

EXAMPLE 7

Example 6 is repeated with the following changes:
12.6 g (0.15 mol) of $NaHCO_3$ are employed in place of 15.9 g of $Na_2CO_3$;
300 ml of N-methylpyrrolidone are employed in place of 300 ml of dimethylformamide,
the reaction temperature is kept at 70° C.
The yield of the compound, according to the invention, of the formula Ib ss 49% of theory by weight. (It is possible to isolate 39% by weight of unreacted $CF_3(CF_2)_5$—$CH_2$—$CHI$—$CH_2OH$, relative to $CF_3(CF_2)_5$—$CH_2$—$CHICH_2OH$ employed, from the diethyl ether washings.)

EXAMPLE 8

Example 6 is repeated with the following changes:
11 g (0.11 mol of $KHCO_3$ are employed in place of 15.9 g of $Na_2CO_3$;
the reaction temperature is kept at 55° to 60° C.;
the reaction duration is limited to 8 hours.
The yield of the compound, according to the invention, of the formula Ib is 44% of theory by weight.

The constitution of the polyfluorinated cyclic carbonates, according to the invention, prepared in the examples was determined by $^1H$ NMR, $^{13}C$ NMR and $^{19}F$ NMR spectroscopy, by IR spectroscopy and by elemental analysis.

In Examples 9 and 10 which follow, the conversion of the polyfluorinated cyclic carbonates according to the invention into the valuable (perfluoroalkyl)-propenols is described in greater detail.

EXAMPLE 9

Conversion of the carbonate, according to the invention, of Example 2 into the perfluoroalkylpropenol of the formula $CF_3(CF_2)_5$—$CH$=$CH$—$CH_2OH$: 42.0 g (0.1 mol) of the carbonate, according to the invention, of the formula Ib (cf. Example 2), 1.0 g (0.01 mol) of $KHCO_3$ and 200 ml of dimethylacetamide are introduced into a 500 ml three-necked flask equipped with reflux condenser, stirrer and thermometer. The mixture is stirred at 90° C. for 12 hours until the evolution of $CO_2$ has ceased. The flask contents are cooled to room temperature, and 0.5 liter of water is added. The lower liquid phase is separated off, extracted several times by stirring with water, and distilled (boiling point: 83° to 85° C. at about 10 mbar). The distillate comprises $CF_3(CF_2)_5$—$CH$=$CH$—$CH_2OH$. The yield is 92% of theory by weight.

EXAMPLE 10

Conversion as in Example 9, $NaHCO_3$ being employed in place of $KHCO_3$ and the dimethylacetamide being omitted. 21.0 g (50 mmol) of the carbonate according to the invention and 0.25 g (3 mmol) of $NaHCO_3$ are introduced into a 100 ml flask fitted with reflux condenser and magnetic stirrer. The mixture is heated to 150° C., and the melt produced is stirred for 6 hours until the evolution of $CO_2$ has ceased. The flask contents are then distilled in vacuo. The yield of $CF_3(CF_2)_5$—$CH$=$CH$—$CH_2OH$ is 81% of theory by weight.

I claim:

1. A polyfluorinated cyclic carbonate of the formula I below

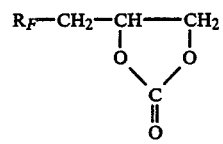

in which $R_F$ is an unbranched or branched perfluoroalkyl radical having 1 to 18 carbon atoms, an unbranched or branched ω-hydro- or ω-bromo- or ωiodoperfluoroalkyl radical having 1 to 18 carbon atoms, or a cycloperfluoroalkyl radical having 4 to 6 carbon atoms.

2. A polyfluorinated cyclic carbonate as claimed in claim 1, where $R_F$ is an unbranched or branched perfluoroalkyl radical having 3 to 14 carbon atoms.

3. A polyfluorinated cyclic carbonate as claimed in claim 1, where $R_F$ is an unbranched perfluoroalkyl radical having 3 to 14 carbon atoms.

* * * * *